United States Patent [19]

Cole et al.

[11] Patent Number: 5,529,920

[45] Date of Patent: * Jun. 25, 1996

[54] HUMAN LIVER EPITHELIAL CELL LINE AND CULTURE MEDIA THEREFOR

[75] Inventors: Katharine H. Cole, Dayton; John F. Lechner, Bethesda, both of Md.; Roger Reddel, Camperdown, Australia; Curtis C. Harris, Bethesda, Md.; Andrea M. Pfeifer, Pyrbaum, Germany

[73] Assignee: The United States of America as represented by the Secretary of the Department of Health and Human Services, Washington, D.C.

[*] Notice: The portion of the term of this patent subsequent to Mar. 3, 2012, has been disclaimed.

[21] Appl. No.: 879,165

[22] Filed: May 1, 1992

Related U.S. Application Data

[63] Continuation-in-part of Ser. No. 844,873, Mar. 3, 1992, Pat. No. 5,342,777, which is a continuation of Ser. No. 377,967, Jul. 11, 1989, abandoned, which is a continuation of Ser. No. 284,331, Dec. 14, 1988, abandoned, and a continuation of Ser. No. 284,368, Dec. 14, 1988, abandoned.

[51] Int. Cl.$^6$ ............... C12N 5/06; C12N 5/10; C12Q 1/02; A01N 63/00
[52] U.S. Cl. ............ 435/240.2; 424/9.2; 424/93.1; 435/4; 435/7.21; 435/6; 435/69.1; 435/240.21; 435/172.3; 435/240.3; 435/240.31; 435/320.1; 935/55; 935/57
[58] Field of Search ............... 435/4, 6, 172.3, 435/240.2, 240.21, 240.31, 7.1, 69.1, 240.3; 424/9.2; 935/55, 57

[56] References Cited

U.S. PATENT DOCUMENTS

| | | | |
|---|---|---|---|
| Re. 30,985 | 6/1982 | Cartaya | 435/240.31 |
| 4,393,133 | 7/1983 | Knowles et al. | 435/6 |
| 4,885,238 | 12/1989 | Reddel et al. | 435/29 |

OTHER PUBLICATIONS

Salas–prato et al. In Vitro Ce . . & Devlop. Bio. 24, 3, pt.1 1988.

Ballet et al, Heratology 4, No. 5, 849–854, 1984.

Bucher, Regulation of Liver Growth: Historical Perspectives and Future Directions, 1987.

Luetteke et al, Control of Hepatocyte Proliferation in Vitro.

Strom et al. Genotoxicity Studies W/ Human Hepatocytes 1987.

Sells et al, In Vitro Cell. & Dev. Bio. 21, No. 4. Apr. 1985.

Chessebeuf et al, In Vitro 20, No. 10, Oct. 1984.

Cruise et al, J. of Cell. Phys. 125:45–50 (1985).

"Instructions to Authors" (Information for Contributors) Cell, 1984.

Amstad et al., Molecular Carcinogenesis 1:151–160 (1988).

DiPaolo, JNOI, vol. 70, No. 1, Jan. (1983).

Mole et al. 1982 Cell 31:11–24.

Lescoat et al, "Influence of Ornithine on Albumin Synthesis by Fetal and Neonatal Hepatocytes Maintained in Culture", Biol. Abs. 84(6)#57462, Sep. 15, 1987.

Van Zoelen et al "Phenotypic Transformation of Normal Rat Kidney Cells in a Growth Defined Medium: Induction by Neurblastoma–Derived Transforming Growth Factor Independently of the Epidermal Growth Factor Receptor", Biol. Abs. V80(3) Aug. 1, 1985 #23,550.

Hoshi et al, "Production of an Auto–Stimulatory Growth Factor by Human Hepatoma Cells Abrogates Requirement for a Brain–Derived Factor" In Vitro Cellular and Developmental Biology, V.21(2), 125–128, Feb. 1985.

Kaighn et al, "Production of Albumin and Other Serum Proteins by Clonal Cultures of Normal Human Liver", PNAS, V. 68, 2396–2400, 1971.

Woodworth et al, "Transformation of Rat Hepatocytes by Transfection with Simian Virus 40 DNA to Yield Proliferating Differentiated Cells," Cancer Res. V. 46, 4018–4026, Aug., 1986.

Hsu et al, "Isolation and Culture of Hepatocytes from Human Liver of Immediate Autopsy" In Vitro, V. 21, 154–160, 1985.

Brash et al, Molecular and Cellular Biology, V.7, 2031–2034, May, 1987.

Lechner et al, "Clonal Growth of Normal Adult Bronchial Epithelial Cells in a Serum–Free Medium," In Vitro, V.18, 633–642, 1982.

Ledley et al, "Retroviral Gene Transfer into Primary Hepatocytes: Implications for Genetic Therapy of Liver–Specific Functions", PNAS, V.84, 5335–5339, Aug., 1987.

Miles Laboratories, Inc., "Ex–cyte" Brochure, 1986.

Reid, "Cloning", Methods in Enzymology, V.LVIII, pp. 152–164, 1979.

*Primary Examiner*—Jasemine C. Chambers
*Assistant Examiner*—Brian R. Stanton
*Attorney, Agent, or Firm*—Birch, Stewart, Kolasch & Birch

[57] ABSTRACT

The present invention relates to long term multiplication and permanent establishment of a cell line of human liver epithelial cells(hepatocytes). The human liver epithelial cell line is capable of mitotically proliferating and continuously growing in vitro under suitable environmental conditions in suitable culture media. A method of producing an immortalized human liver epithelial cell line is also disclosed. The invention also relates to serum-free cell medium developed to support long term multiplication and permanent establishment of a cell line of human liver epithelial cells. The medium may contain an effective cell growth promoting amount of calcium ions; an effective cell growth promoting amount of glucose; an effective amount of insulin to aid cells in glucose uptake; an effective cell growth promoting amount of hydrocortisone; an effective amount of epidermal growth factor to bind epidermal growth factor receptors on cells; an effective amount of transferrin to increase DNA synthesis in cells; an effective amount of cholera toxin to increase DNA synthesis in cells; an effective amount of triiodothyronine to increase DNA synthesis in cells; and an effective growth promoting amount of mammalian hormones and mitogenic factors, including lipoprotein, cholesterol, phospholipids and fatty acids.

22 Claims, 1 Drawing Sheet

HUMAN LIVER EPITHELIAL CELL LINE AND CULTURE MEDIA THEREFOR

CROSS REFERENCE TO RELATED APPLICATIONS

This application is a continuation-in-part of application No. 07/844,873, filed Mar. 3, 1992, now U.S. Pat. No. 5,342,372, which is a continuation of application Ser. No. 07/377,967 filed on Jul. 11, 1989, now abandoned, which is a Continuation of application Ser. Nos. 07/284,331 filed Dec. 14, 1988 now abandoned and 07/284,368 filed Dec. 14, 1988, now abandoned which are both hereby incorporated by reference.

BACKGROUND OF THE INVENTION

Normal human hepatocytes are extremely difficult to obtain due to their rapid decrease in viability following autopsy. Additionally, the human liver is one of the few organs in adults capable of regeneration. However, replicative cultures of adult human hepatocytes have never been adequately established. These cells have a very limited lifespan when put into cell culture.

There are several examples of animal liver cell cultures derived from experimental laboratory animals such as rats (Tsao et. al., *Exp. Cell Res.*, 154:38–52 (1984); Enat et al., "Proc. Nat Acad. Sci USA", 87: 1411–1415 (1984)). Rat liver epithelial cells from adult rat liver tissue have been established using serum free medium (Chessebeuf and Padieu, *In Vitro*, 20, 780–795 (1984); Enat et al, *Proc. Natl. Acad. Sci.*, 81, 1411–1415 (1984)). Rat liver cells have been transformed by transfection with SV40 DNA (Woodworth et al, *Cancer Res.*, 46: 4018–4026 (1987); Ledley et al., *Proc. Nat. Acad. Sci. USA*, 84: 5335–5339 (1987) but those cells are not suitable for human drug metabolism or carcinogenesis studies because of xenobiotic metabolism differences between rat and human liver cells.

Clonally-derived cultures of human hepatocytes have been reported (Kaighn and Prince, *Proc. Nat. Acad. Sci.*, 68, 2396–2400 (1971)), but no new data has been generated to support or refute these observations. In addition, the medium used contained 17% serum. Several studies have shown that serum (Hashi and Carr *J. Cell Physiol.*, 25, 82–90 (1985)), and more specifically transforming growth factor-beta (TGF-β) present in serum (Nakaruma et al., *Biochem. Biophys. Res. Commu.*, 133, 1042–50 (1985); Lin et al., *Biochem. Biophys. Res. Commu.*, 143, 26–30 (1987); and Strain et al., *Biochem. Biophys. Res. Commu.*, 145, 436–442 (1987)) cause a marked decrease in DNA synthesis of rat hepatocytes in culture. Serum was also found to cause undesired cellular differentiation and retarded replication.

Long-Term cultures of human fetal liver have been established (Salas-Prato, M. et al, *In Vitro Cell Dev. Biol.*, 24:230–238 (1988); Sells, M. A. et al, *In Vitro Cell Dev. Biol.*, 21:216–220 (1985)), however the inherent differences between fetal and adult liver, especially in the area of xenobiotic metabolism make adult hepatocytes a more suitable model for carcinogenesis and toxicity studies.

Rat liver epithelial cells from adult rat liver tissue have been established using serum-free medium (Chessebeuf and Padieu, *In Vitro*, 20, 780–795 (1984); Enat et al., *Proc. Natl. Acad. Sci.*, 81, 1411–1415 (1984)).

Human hepatoma cell lines have been cultured and are available (e.g. Knowles et al., U.S. Pat. No. 4,393,133, Jul. 12, 1983, Human Hepatoma Derived Cell Line) but, are not usable in carcinogenesis studies because they are tumorigenic. They were also cultured in medium containing serum.

The medium described herein contains chemically denatured serum (Van Zoelen, E. J. J., *J. Cell Physiol.*, 123:151–160 (1985)) that contains no active TGF-β which we concluded inhibited DNA manufacture and cell division. This medium the uses cholera toxin, bovine pituitary extract and chemically denatured serum.

Prior cell lines have serious limitations because they are not of human origin, or are not more closely representative of normal human liver cell.

SUMMARY OF THE INVENTION

It is, therefore, an object of the present invention to produce a normal adult and neonatal human liver epithelial cell line or derivative thereof with extended life span growing in an in vitro culture growth medium. These new cell may be used for research that will more reliably predict the effect of various chemical assaults on the cell in carcinogen and mutagen research, metabolism research and other applications for cell lines.

It is a further object of the invention to produce a cell line which can be used in experiments that require large numbers of homogenous (identical and cloned) cells for: drug metabolism studies; evaluating chemical compounds which require liver metabolism for functional activation; chemical carcinogenesis studies with the potential for screening compounds with human carcinogenic and or tumor promoting potential; investigation of controls of differentiation for possible use with liver anti-cancer drugs which act by inducing terminal differentiation; growth of Hepatitis virus in replicating hepatocytes; growth of human parasites; and transfection of additional oncogenes to evaluate their effect on these cells. Cultures of human hepatocytes can provide a more relevant view of human liver metabolism and disease process than data obtained from hepatocyte cultures derived from other animal species.

These objects are accomplished by culturing normal human hepatocytes from immediate autopsy liver tissue (as described by Hsu et al., *In Vitro Cell Develop. Biol.*, 21: 154–160 (1985)). The cells, in culture for 24 hours, were transfected with recombinant plasmid containing SV40 virus large T antigen gene driven by Rous sarcoma virus long terminal repeat, p-RSV-T (Brash et al., *Molec. Cell Biol.*, 2031–2034 (1987)). Foci (transformed colonies) of the transformed cells formed within 6–8 weeks following transfection.

These cells were trypsinized and serially passaged and subsequently expanded into cultures of cells. The cells were characterized and found to be positive for cytokeratin and T-antigen gene expression. The cells have been subcultured 10 times and have undergone more than 40 replications. The transformation frequency of cultured liver epithelial cells was $1\times10^{-4}$.

Attempts to clone single cells or foci from the original or later cultures resulted in death of the cells within 2–3 days after the cells were moved. Thereafter, the flasks were serially passaged. The first two passages following foci appearance were subcultured using the collagenase/Dispase solution used for original isolation, due to the extreme sensitivity of the cells to trypsin, and the remaining passages were done with the PVP-trypsin-EDTA solution. Dispase (0.5 U/mg) was obtained from Boehringer Mannheim (Indianapolis, Ind.), collagenase (156 U/mg) from Worthington Biochemical Corp. (Freehold, N.J.) and standard tissue culture media and components from Biofluids Inc. (Rockville, Md.). Epidermal growth factor was obtained from Collaborative Research Inc. (Bedford, Mass.). Trypsin inhibitor, DNase and chemicals were obtained from Sigma Chemical Co. (St. Louis, Mo.). PFMR4 cell culture medium and factor free serum were prepared by Biological Research Faculty and facility (Ijamsville, Md.). With increasing passage, the cells became more homogeneous, and at the 5th passage following transfection, virtually 100% of the cells expressed SV40 large T antigen.

Since the initial transfection, these cells have been subcultured 11 times, have undergone greater than 40 replications, have a generation time of 48 hrs and a colony forming efficiency of 25%.

As described in the following example, the normal human liver epithelial cells can be made to grow continuously by transfecting the cells with the T antigen gene of SV40 virus. Transfection or infection can be accomplished by use of a virus or a plasmid containing the T antigen gene of the SV40 virus. Either transfection or infection may lead to transformation of the cell line. Other transformation vectors may also be useful, such as papilloma virus or Epstein Barr virus. The techniques for making continous human cell lines are described in the following references: Grahm. F. L., Smiley J., Russell, W. C. and Nairn, R. Characteristics of a human cell line transformed by DNA from human adenovirus type 5. *J. Gen. Virol.*, 36:59–72 (1977); Zur Hausen, H. Oncogenic herpes viruses In: J. Tooze (ed.), DNA tumor viruses, Rev. Ed. 2, pp 747–798. Cold Spring Harbor, N.Y., Cold Spring Harbor Press (1981); Popovic, M., Lange-Wantein, G., Sarin, P. S., Mann, D. and Gallo, R. C. Transformation of a human umbilical cord blood T-cells by human T-cell leukemia/lymphon virus (HTLV), *Proc. Natl. Acad. Sci. USA*; DiPaolo, J. A. Pirisi, I., Popeseu, N. C., Yasumoto, S., Poniger, J. Progressive changes induced in human and mouse cells by human Papillomavirus Type-16 DNA, Cancer Cells 5:253–257 (1987).

It is another object of the present invention to provide an improved aqueous culture medium to produce a normal human liver epithelial cell line that is prolific, enduring and has an unlimited life span in culture. As a result, it has been found that a suitable basic culture medium which provides nutrients may be modified with the addition of insulin, epithelial growth factor (EGF), hydrocortisone, transferrin, cholera toxin, aqueous bovine pituitary extract (Lechner, J. and Laveck, M. J., J. Tissue Cult. Method, 9, 43–48 (1985)), denatured serum and HepG2 conditioned medium (Hoshi, H. and McKeehan, W. L., *In Vitro Cell Dev. Biol.*, 21:125–128 (1985)) accomplishes the intended result. The medium described herein contains chemically denatured serum that contains no active TGF-β.

It is a further object of the invention to produce a cell culture medium containing ornithine, fatty acids, insulin, EGF, hydrocortisone, transferrin, cholera toxin, aqueous pituitary extract and denatured serum added to commercially available PFMR4 medium (without arginine), conditioned with medium from HepG2 hepatoma cells for liver cell lines which can be used in experiments that require large numbers of homogenous (identical and cloned) cells for: drug metabolism studies; evaluating chemical compounds which require liver metabolism for functional activation; chemical carcinogenesis studies with the potential for screening compounds with human carcinogenic and/or tumor promoting potential; investigation of controls of differentiation for possible use with anti-liver cancer drugs which act by inducing terminal differentiation; growth of Hepatitis virus in replicating hepatocytes; growth of human parasites; and transfection of additional oncogenes to evaluate their effect on these cells.

The above objects of the invention have been substantially achieved by the development of an improved serum-free culture medium. The culture medium is prepared using the basal medium PFMR4 (described in Lechner et al, *Methods in Cell Biol.*, 21, 195 (1980)) with arginine, calcium, glutamine, trace elements and iron not included.

The culture medium used during transfection or immortalization of the cell line should contain an effective cell growth promoting amount of calcium ions; an effective cell growth promoting amount of glucose; an effective amount of insulin to aid cells in glucose uptake; an effective cell growth promoting amount of hydrocortisone; an effective amount of epidermal growth factor to bind epidermal growth factor receptors on cells; an effective amount of transferrin to increase DNA synthesis in cells; an effective amount of cholera toxin to increase DNA synthesis in cells; an effective amount of triiodothyronine to increase DNA synthesis in cells; and an effective growth promoting amount of mammalian hormones.

In a more preferred embodiment of the invention the mammalian cell culturing medium contains an effective cell growth promoting amount of the essential amino acids; an effective cell growth promoting amount of water soluble vitamins; an effective cell growth promoting amount of coenzymes; an effective cell growth promoting amount of sodium ions; an effective cell growth promoting amount of calcium ions; an effective cell growth promoting amount of glucose; an effective amount of insulin to aid cells in glucose uptake; an effective cell growth promoting amount of hydrocortisone; an effective amount of epidermal growth factor to bind epidermal growth factor receptors on cells; an effective amount of transferrin to increase DNA synthesis in cells; an effective amount of cholera toxin to increase DNA synthesis in cells; an effective amount of triiodothyronine to increase DNA synthesis in cells; an effective amount of retinoic acid to increase DNA synthesis in cells; and an effective growth promoting amount of mammalian hormones.

In a most preferred embodiment of the invention the cell culturing medium is an aqueous cell culturing medium suitable for culturing normal adult human liver epithelial cells which contains water; an effective cell growth promoting amount of all of the essential amino acids; an effective cell growth promoting amount of water soluble vitamins; an effective cell growth promoting amount of coenzymes; an effective cell growth promoting amount of sodium ions; an effective amount of calcium ions high enough to promote cell growth but low enough to avoid cellular differentiation; an effective cell growth promoting amount of glucose; insulin in an amount of 1 to 10 µg/ml; hydrocortisone in an amount of 0.05 to 1 µM; epidermal growth factor in an amount of 1 to 25 ng/ml; transferrin in an amount of 1 to 10 µg/ml; cholera toxin in an amount of 5 to 50 ng/ml; triiodothyronine in an amount of 1 to 100 nM; retinoic acid in an amount of 1 to 300 nM; an effective amount of a mammalian pituitary extract to provide hormones necessary for culturing normal adult human liver epithelial cells; an effective cell growth promoting amount of conditioned medium derived from HepG2 hepatoblastoma cells or a mutant thereof; and an effective amount of a buffer to maintain the pH between 6.7 and 7.6.

The glucose is an energy source for the cells and is preferably present in an amount of 0.5 to 0.5 mg/ml. Insulin should also be included in an amount sufficient to aid the cells in glucose uptake. This amount is preferably 1 to 10 µg/ml.

The hydrocortisone, cholera toxin and retinoic acid are potentially toxic and therefore should be present in amounts sufficient to achieve their desired effects, but low enough to inhibit cell growth due to the inherent toxicity of these materials.

The epidermal growth factor, transferrin, cholera toxin, triiodothyronine, retinoic acid and bovine pituitary extract aid DNA synthesis. Mitogenic factors should be present in an amount sufficient to aid DNA synthesis.

The pH of the culturing medium may be adjusted to achieve an optimal effect depending on the cell line to be cultured. The pH is usually between 6.7 and 7.6, preferably 7.0 and 7.4, more preferably 7.1 to 7.3, and most preferably about 7.2.

The bovine pituitary extract is present in an amount sufficient to provide the necessary hormones for cell growth. The bovine pituitary extract may be present in an amount of 0.75 to 75 µg/ml.

The culture medium should contain a source of an aqueous mixture of lipoprotein, cholesterol, phospholipids and fatty acids with low endotoxin. A suitable source of these ingredients is EX-CYTE®V sold by Miles Inc. The Ex-cyte products including V have the following characteristics:

Animal virus and mycoplasma free.

Certification of freedom from animal viruses and mycoplasma available.

All components heat-treated equivalent to 10 hr. at 60° C.

Contains no IgG or IgM.

Water soluble.

Low level of endotoxin.

Stable for years at −20 degrees C. EX-CYTE® products are unique aqueous (or water soluble) lipoprotein fractions that cause the modulation of cell membrane proteins. They are a mixture of lipoprotein cholesterol, phospholipids, and fatty acids and consequently are a source of lipids the cells can use to design membrane structure and optimize surface protein positioning. Idealized protein orientation can enhance membrane receptor accessibility and permeability of solutes. In addition, by supplying the cells with the preformed cholesterol and phospholipids, the cells need not biosynthesize the lipids from base ingredients such as exogenous fatty acids. Fortification with the transport proteins, albumin and transferrin, provides cells with many of the factors required for growth with basal media. The fatty acids are an energy source for liver cells for DNA synthesis when the cells start to divide. The EX-CYTE should be present in an amount of 100 to 1500 µg/ml, preferably 150 to 500 µg/ml, most preferably about 312 µg/ml.

The Ex-cyte products have the following general composition:

TABLE I

CHARACTERISTICS

| | Lipoprotein Profile of EX-CYTE | | | Human |
|---|---|---|---|---|
| | Bovine Cholesterol (mg/mL) | Triglycerides (mg/mL) | Cholesterol (mg/mL) | Triglycerides (mg/mL) |
| Total: | 9.48 | 0.05 | 5.24 | 2.87 |
| VLDL: | 0 | 0 | 0.40 | 1.07 |
| LDL: | 3.36 | 0.03 | 4.80 | 1.78 |
| HDL: | 6.12 | 0.02 | 0.04 | 0.02 |

Phospholipid Profile of EX-CYTE

TABLE I-continued

| | Bovine | Human |
|---|---|---|
| Total Phospholipids, mg/mL | 10.53 | 5.54 |
| Phosphatidyl Choline, mg/mL | 7.15 | 2.49 |
| Lysophosphatidyl Choline, mg/mL | 0.93 | 0.69 |
| Sphingomyelin, mg/mL | 2.34 | 2.36 |
| Phosphatidyl Ethanolamine, mg/mL | 0.02 | 0 |
| Total Cholesterol, mg/mL | 9.48 | 5.24 |
| Cholesterol, Phospholipid Ratio | 0.90 | 0.95 |

Free Fatty Acid Analysis of EX-CYTE

| | Bovine |
|---|---|
| Total Cholesterol | 15.2 mg/mL |

| Fatty Acid | Approx. Conc. µg/ml | µg fatty acid/ mg cholesterol |
|---|---|---|
| Linoleic, C 18:2 | 546 | 35.9 |
| Palmitic, C 16 | 233 | 15.3 |
| Oleic, C 18:1 | 156 | 10.3 |
| Stearic, C 18 | 348 | 22.9 |

A broad spectrum antibiotic such as gentamicin and antimycotic agent may be included in the culture medium to prevent bacterial, yeast, fungal or other contamination.

The present invention is also directed to a method for culturing various types of mammalian cells, including normal adult human liver epithelial cells as well as other types of human cells, which comprises culturing the cells in the above-described culturing medium.

Normal human adult liver cells are cultured at a density sufficient to allow cell growth. Typical concentrations are $5\times10^1$ to $1\times10^4$ cells/cm$^2$ of surface area of the cell culture container, preferably $5\times10^2$ to $3\times10^3$ cells/cm$^2$, most preferably about $1.3\times10^3$ cells/cm$^2$. The cells are cultured under aerobic moist conditions at a temperature between 33° to 40° C. preferably about 37° C. The cell culture is passaged as the cells approach confluence on the surface on which they are being cultured. The normal human adult liver cells can be cultured for at least two rounds of DNA synthesis, preferably at least 5 rounds of DNA synthesis and more preferably at least 10 rounds of DNA synthesis. Transformed cells can be cultured under much less restrictive or controlled conditions.

The present invention is also directed to a kit for screening carcinogenic or chemotherapeutic agent comprising a container containing non-tumorigenic, human liver cell line or derivative thereof growing continually when cultured in vitro in growth medium.

The present invention is also directed to a method for testing carcinogenicity of an agent, comprising culturing the above-described cell line with an agent suspected of being carcinogenic; and determining formation of abnormal cellular mass by said cell line, the formation of abnormal cellular mass being indicative of carcinogenicity of said agent.

The present invention is also directed to a method for testing antineoplastic activity of an agent, comprising culturing the above-described cell line with a potential antineoplastic agent, and determining growth of said cell line, a lack of growth of said cell line being indicative of antineoplastic potency of said agent.

The present invention is also directed to a method for testing carcinogenic promotion of an agent, comprising culturing the above described cell line with an agent of known carcinogenic initiation capability, then subsequently exposing these cells to an agent suspected of being a neoplastic promotor. Formation of abnormal cellular mass following promoting agent and not following initiating agent being indicative of neoplastic promotion by said agent.

These and other objects, features and advantages of the invention will be better understood upon a reading of the following detailed description when considered with the accompanying drawing.

DETAILED DESCRIPTION OF THE INVENTION

Figure 1:
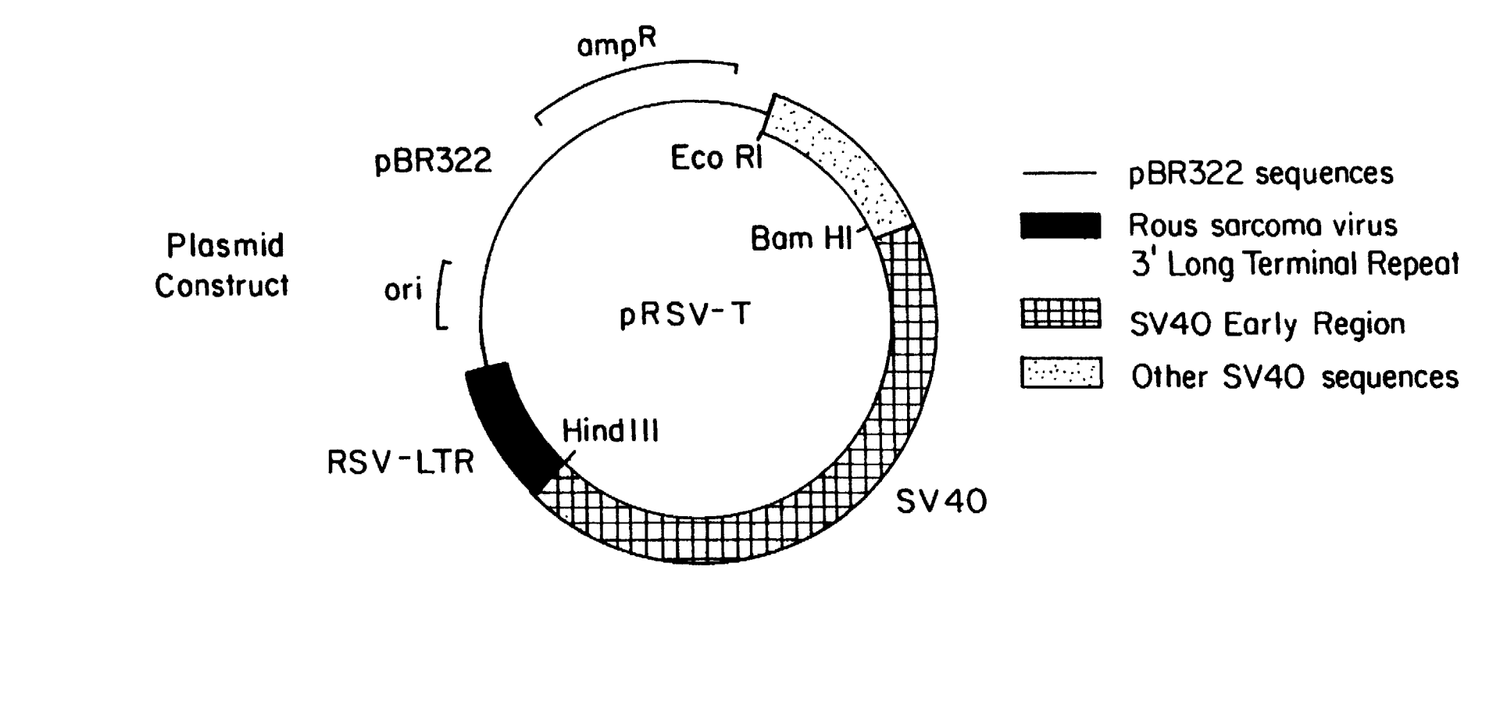
FIG. 1 shows a representation of the plasmid used to transfect normal human hepatocytes from immediate autopsy liver tissue. The cells were transfected with the recombinant plasmid containing SV40 virus large T antigen gene driven by Rous sarcoma virus long terminal repeat, p-RSV-T (Brash et al., *Molec. Cell Biol.*, 2031–2034 (1987)).

Unless defined otherwise, all technical and scientific terms used herein have the same meanings commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference.

The term "continuous cell line" as used herein means that the cell line grows continually without senescence when cultured in vitro in a suitable growth medium.

The "derivatives" of the liver cell line(s) of the present invention include cells which have been further genetically altered by adding, for example, genes for drug metabolizing enzymes, other oncogenes, anti-oxidant genes, etc. thereby creating a continuous derivative of the cell line.

The term "immortalized" as used herein means that the cell line grows continually without senescence when cultured in vitro in a suitable growth medium.

The successful culturing of liver epithelial cells in the medium of the present invention results from the unexpected finding that ornithine, fatty acids, insulin, EGF, hydrocortisone, transferrin, cholera toxin, aqueous pituitary extract and denatured serum and conditioned with HepG2 medium to provide factors necessary in the successful proliferation of liver cells.

General Method for Preparation of the Basic Medium

Basal PFMR4 medium prepared is as described in Lechner, J. F. et al. Normal human prostate epithelial cell cultures are described in Harris, C. C., Trump, B. F., Stoner, G. D. (eds) *Methods in Cell Biology*, Vol. 21B, Academic Press, New York, pp. 195–225.

General Method for Construction of Cell Lines

Normal human hepatocytes were cultured from immediate autopsy liver tissue (as described by Hsu et al., *In Vitro Cell Develop. Biol.*, 21: 154–160 (1985)). The cells in culture for 24 hours were transfected with recombinant plasmid containing SV40 virus large T antigen gene driven by Rous sarcoma virus long terminal repeat, p-RSV-T (Brash et al., *Molec. Cell Biol.*, 2031–2034 (1987) and Reddel et al, *Cancer Research*, 48, 1904–1909 (1988)). The cells were easily recognized morphologically using phase contrast microscopy. Foci of the transformed cells were trypsinized and serially passaged. The cells were characterized and found to be positive for keratin and T-antigen expression. In all cases the life span of the cell cultures was considerably increased to as many as 40 to 50 cell divisions. In all cases the life span of the colonies of cells transformed was extended as compared to normal liver epithelial cell cultures. The p-RSV-T has been transfected into human mesothelial cells (R. R. Reddel, submitted) human prostate epithelial cells (M. E. Kaighn, J. F. Lechner, and R. R. Reddel, submitted) and human bronchial epithelial cells (R. R. Reddel et al, *Can. Res.*, 48:1904–1909 (1988)).

During culturing most of the cells underwent a long period (3 to 4 months) of senescence, referred to as "crisis" in which time replication ceased. With continued culture some of the cells are expected to survive and replicate showing an unlimited potential for growth.

Expression of SV40 large T antigen: Cells were grown on tissue culture chamber slides (Lab-Tek). The cells were fixed in absolute methanol at 4° C. for 30 min. Indirect immunofluorescence was done by exposing cells to a monoclonal antibody for SV40 large T antigen (Oncogene Science, Mineola, N.Y.) for 30 min at room temperature followed by a secondary anti-mouse immunoglobulin labeled with either fluorescein isothiocyanate (FITC) or tetramethyl rhodamine isothiocyanate (TRITC).

Expression of albumin, keratin, $\alpha$ fetoprotein, $\alpha$ 1 antitrypsin, $\alpha$ 2 macroglobulin: Cells were grown on Lab-Tek slide chambers. The cells were fixed by immersion of rinsed slides in a phosphate buffer containing 4 parts formaldehyde and 1 part glutaraldehyde for 1 hr to determine expression of albumin, $\alpha$ fetoprotein, $\alpha$ 1 antitrypsin and $\alpha$ 2 macroglobulin, or fixed in 100% methanol for 30 min for keratin expression. The slides were washed and the appropriate blocking serum was placed on the slides for 30 min. The primary antibody (IgG) against albumin (1:25), $\alpha$ fetoprotein (1:20), $\alpha$ 1 antitrypsin, $\alpha$ macroglobulin (1:20), general cytokeratin (1:15) and cytokeratin 18,19 (1:20) were applied to slides and incubated for 1 hr at 37° C. Secondary antibodies labeled with FITC or TRITC were placed on rinsed slides at a dilution of 1:32 for 1 hr at 37° C.

Clonal growth assay: The ability of transformed liver epithelial cells to undergo clonal growth was determined according to methods previously described. Monolayer cultures were dissociated into single cells and clonal cultures were initiated by seeding 1000 cells/60 mm dish (100 cells/cm$^2$) whose surface had been coated with collagen. After 10 days in culture, the cells were fixed with 10% formalin and stained with 0.25 crystal violet. The growth rate was defined as average population doublings/clone/day, as measured by the log 2 of the number of cells in 20 randomly selected colonies.

DNA synthesis assay: Transformed liver epithelial cells (TLE) were seeded at clonal density (200 cells/cm$^2$) onto collagen coated Costar 6 well dishes. After 24 hrs of culture, the culture medium was supplemented with 0.5 µCi if [$^3$H]thymidine/ml. After 24 hrs of growth, the medium was removed and the cells were washed with a phosphate buffered saline solution and dissolved in 1 ml of 0.2 NaOH containing 40 µg/ml of calf thymus DNA. This cell-NaOH mixture was then poured onto Whatman 25 mm GF/C acid soaked glass filters. The filters were then rinsed with 1N HCl followed by a rinse with 95% ethanol. The radioactivity was quantified using an LKB scintillation counter. Assays were performed in triplicate.

EXAMPLE 1 (PREPARATION OF MEDIUM)

The medium was prepared in three steps. Step 1 was the preparation, by a commercial source of "basic medium" which contains the basic nutrients and some other components. The second step was the addition to the medium of various key ingredients and salts which if included in the "basic medium" when prepared by the commercial source would curtail the shelf life of the product. Therefore, Step 2 is usually conducted only shortly before the medium is to be used. The third step was the conditioning of the medium on certain cells to extract factors which are essential for the medium.

The medium is formulated in accordance with good laboratory procedure as known in the art.

TABLE II

1. Basic Medium
The formula is as follows:
A custom basal medium PFMR4 (Lechner et al, Methods in Cell Biol., 21, 195 (1980)) is commercially available from facilities such as Biological Research Faculty & Facility, Inc., Ijamsville, MD 21754. The custom medium used omitted certain ingredients specified in Lechner, above, e.g., arginine (has been taken out of the base medium because fibroblasts present in the original isolation cannot live without arginine and so the culture becomes almost totally hepatocytes), calcium (has been used at different concentrations so it is not added into the original medium), glutamine (left out due to shelf life degradation of the glutamine), trace elements and iron (tend to precipitate out of solution after long periods of time so they are added fresh). The main reason for the omission is to obtain a longer shelf life for the "basic medium".

| The custom basal medium contains: | |
|---|---|
| INGREDIENT | mg/liter |
| Essential Amino Acids | |
| L-Cystine.2HCl | 47.0 |
| L-Histidine | 41.9 |
| L-Isoleucine | 7.9 |
| L-Leucine | 26.2 |
| L-Lysine.HCl | 73.0 |
| L-Methionine | 9.0 |
| L-Phenylalanine | 9.9 |
| L-Threonine | 23.8 |
| L-Tryptophan | 4.1 |
| L-Tyrosine.2Na.2H$_2$O | 15.7 |
| L-Valine | 23.4 |
| Nonessential Amino Acids | |
| L-Alanine | 17.8 |
| L-Asparagine.H$_2$O | 30.0 |
| Aspartic Acid | 26.6 |
| Glutamic Acid | 29.4 |
| L-Glycine | 15.0 |
| L-Proline | 69.1 |
| L-Serine | 21.0 |
| or derivatives | |
| Amino Acid Derivatives | |
| Putrescine.2HCl | 0.32 |
| Water Soluble Vitamins and Coenzymes | |
| d-Biotin | 0.07 |
| Folic Acid | 1.32 |
| DL-A-Lipoic Acid (Thioctic) | 0.21 |
| Nicotinamide | 0.04 |

TABLE II-continued

| | |
|---|---|
| D-Pantothenic Acid | 0.24 |
| Pyridoxine.HCl | 0.06 |
| Riboflavin | 0.04 |
| Thiamine.HCl | 0.34 |
| Vitamin B12 (Cynacobalamine) | 1.36 |
| Carbohydrate/Derivatives | |
| Pyruvic Acid | 174.0 |
| Sodium Acetate | 295.6 |
| Nucleic Acid Derivatives | |
| Hypoxanthine | 4.1 |
| Thymidine | 0.7 |
| Lipids/Derivative | |
| Choline Chloride | 14.0 |
| i-Inositol | 18.0 |
| Bulk Inorganic Ions (Salts) | |
| NaCl | 5844.0 |
| KCl | 283.3 |
| Na$_2$HPO$_4$ | 126.4 |
| KH$_2$PO$_4$ | 58.5 |
| MgSO$_4$ | 19.3 |
| MgCl$_2$.6H$_2$O | 105.7 |
| Inorganic Trace Elements | |
| CuSO$_4$.5H$_2$O | 0.002 |
| Buffers and Indicators | |
| HaHCO$_3$ | 1176.0 |
| HEPES buffer (Made by Biofluids) | 7149.0 |
| Phenol Red | 1.1 |

TABLE III

2. Additional Substances
To the commercial medium the following substances were added to bring the final concentration to the indicated concentrations:

| Item | Amount |
|---|---|
| L-glutamine | 2 mM |
| insulin | 10 µg/ml |
| hydrocortisone | 0.2 µM |
| epidermal growth factor | 5.0 ng/ml |
| transferrin | 10 µg/ml |
| phosphoethanolamine | 0.5 µM |
| cholera toxin | 25 ng/ml |
| triiodothyronine | 10 nM |
| retinoic acid | 10 nM |
| ornithine | 2 mM |
| CaCl$_2$ | 0.4 mM |
| glucose | 2.0 mg/ml |
| bovine pituitary extract | 7.5 µg/ml |
| "Ex-cyte ® V (Miles Diagnostics, Pentex Products, Kankakee, IL) | 312 µg/ml |
| FeSO$_4$.7H$_2$O | 2.7 µM |
| ZnSO$_4$.7H$_2$O | 0.5 µM |
| Factor Free Serum (Van Zoolen et al., J. Cell Physiol., 123:151 (1985) | 10% |
| Na$_2$SeO$_3$ | $3.0 \times 10^{-8}$M |
| MnCl$_2$.4H$_2$O | 1.0 nM |
| Na$_2$SiO$_3$.9H$_2$O | $5.0 \times 10^{-7}$M |
| (NH$_4$)$_6$Mo$_7$O$_{24}$.4H$_2$O | 1.0 nM |
| NH$_4$VO$_3$ | 5.0 nM |
| NiSO$_4$.6H$_2$O | 0.5 nM |
| SnCl$_2$.2H$_2$O | 0.4 nM |
| Gentamicin | 50 µg/ml |

Unless otherwise indicated, the quantities may be varied by a factor of 1 log or plus or minus 20% depending on toxic effect of the ingredient at higher levels and minimal requirements for growth; which modifications are considered to be "about" those required to function as does the listed formula.

The serum-free medium (growth-factor-inactivated serum) was prepared as follows:

Fetal bovine serum (FBS; Flow Laboratories, Irvine, Scotland) was incubated with 100 mM dithiothreitol (DTT; Boehringer, Mannheim, GFR) for 2 hr at room temperature while stirring, resulting in turbid solution. The suspension was then dialyzed (molecular weight cutoff 8–10 kDa) overnight at 4° C. against a 50–100 fold excess of phosphate-buffered saline without $Ca^{++}$ and $Mg^{++}$ (PBS; 137mM NaCl, 2.7 mM KCl, 6.5 mM $Na_2HPO_4$, 1.5 mM $KH_2PO_4$, pH 7.4). Subsequently iodoacetamine (Sigma, St. Louis, Mo., USA) was added at 5 g/liter, and the suspension incubated for another 2 hr at room temperature while stirring, followed by dialysis for 2 days against several aliquots of PBS, and an additional day against PBS containing in addition 0.9 mM $CaCl_2$ and 0.5 mM $MgCl_2$. Subsequently, the SH-FCS was centrifuged at 25,000 g for 30 min at 4° C., and the supernatant again at 100,000 g for 60 min at 4° C. The clear supernatant was sterilized by passage through a Millex-GV 0.22 nm filter (Millipore, Bedford, Mass., USA). (Prepared from protocol in Van Zoelen et al, *J. Cell Physiol.*, 123, 151–160 (1985)).

The Ex-cyte ® used had the following characteristics-
PENTEX ® EX-CYTE ® V, 50X
Growth Enhancement Media Supplement
Albumin Enriched
(Salt Poor)

| | |
|---|---|
| PROTEIN By Biuret | 786 mg/g powder |
| CHOLESTEROL (1) By Enzymatic Assay | 64.3 mg/g powder |
| SODIUM CHLORIDE | 5.0 mg/g |
| pH (7% Solution) | 7.9 mg/g |
| ENDOTOXIN LEVEL By Limulus Amebocyte Lysate | 0.03 ng/mg |
| MOISTURE By Karl Fischer | Less than 5% when packaged |
| STORAGE | −20° C. or below |
| RECONSTITUTE WITH (2) | Pyrogen-free $H_2O$ or redissolve directly in nutrient medium |

(1) It has been previously determined that there is approximately a 1:1 ratio of phospholipids and cholesterol in EX-CYTE preparations.
(2) 625 mg of powder is sufficient for one liter of final nutrient medium containing 40 μg cholesterol/mL and 0.49 mg albumin/mL. Endotoxin level at working concentration of cholesterol and albumin is 0.02 ng/mL.

The conditioned medium is prepared by placing the HGM medium on medium density monolayer cultures of 1) HepG2 hepatoblastoma cells (American Type Tissue Collection #HB80-65) or 2) Human liver epithelial cells transformed by transfection with SV-40 DNA (NCI/NIH, patent pending) for 72 hours. This conditioned medium is added to normal HGM at a 35% concentration.

EXAMPLE 2 (TRANSFECTED CELLS)

Development of HLC-Cell Line

Normal human hepatocytes were isolated from immediate autopsy tissue from non-cancerous individuals by a combination of perfusion and digestion techniques as described by Hsu et al., *In Vitro Cell Develop. Biol.*, 21:154–160 (1985). The left lobe of the liver was removed from non-cancerous patients within 2 hr of cessation of cardiac function, immersed in ice cold Lebowitz-15 cell medium (L-15) and transported to the site of liver cell isolation.

The hepatocytes were dissociated into cell suspensions by perfusing the liver with a calcium and magnesium free Hank's balanced salt solution containing 0.5 mM EDTA, and 0.05 M Hepes at 37° C. at a flow rate of 30–40 ml/min for 15 min.

The perfusate was then changed to a digestion solution containing collagenase (185–200 U/ml) at 37° C. at a flow rate of 30–40 ml/min for 20 min. The dissociated hepatocytes were purified from debris and red blood cells by 3 successive washes with L-15 and filtration through a 10 μ nylon filter. The hepatocytes were suspended in Waymouth's medium supplemented with 10% fetal bovine serum (FBS), 1 μg/ml insulin and 50 μg/ml gentamicin. The yield estimated counting the cells with a hemocytometer were 1–2× $10^7$ cells/g of liver tissue. Over 90% of the hepatocytes excluded trypan blue.

Following isolation the cells (hepatocytes) were seeded into T-75 tissue culture flasks (Lux, Miles Scientific. Naperville, Ill.) whose surfaces had been coated with collagen (Michalopoulos, G. and Pitot, H. Exp. Cell Res. 94:70–73, yr) (Flow Lab, Rockville, Md.) at 3–5×$10^5$ cells/flask using Waymouth's cell medium with insulin (1 μg/ml), gentamicin (50 μg/ml), and fetal bovine serum (10%).

Twenty-four hours after initial seeding (isolation), the medium was changed to serum-free medium HGM (Hepatocyte Growth Medium) PFMR4 described below. The medium is made without arginine and supplemented with ornithine (2 mM), insulin (10 μg/ml), hydrocortisone (0.2 μM), epidermal growth factor (5 ng/ml), transferrin (10 μg/ml), phosphoethanolamine (0.5 μM), cholera toxin (25 ng/ml), triiodothyronine (10 nM), bovine pituitary extract (7.5 μg/ml) and factor-free serum (10%). Additionally, this medium was supplemented (35%) with conditioned medium obtained by placing medium described above in contact with high density cultures of human hepatoblastoma cell line (HepG2) for 72 hrs.

Forty-eight hours after the original isolation and 3 hours prior to transfection the cells were fed with 10 ml of LHC-9 cell medium (Lechner, J. F. and Laveck, M. A., *Tissue Cult. Method.*, 9:43–48 (1985)). The cells were transfected with a plasmid pRSV-T (obtained from NCI) which contained SV40 ori-construction containing the SV40 early region genes and the Rous sarcoma virus long terminal repeat (LTR). Transfection was accomplished by using the strontium phosphate co-precipitation method described by Brash, D. et al, *Molec. Cell Biol.*, 7:2031–2034 (1987)).

3–5×$10^5$ cells/flask (T-75 cm) were transfected with 10 μg of DNA precipitate at pH 7.8. After two hours of exposure, the hepatocytes were rinsed twice with serum-free cell medium at 37° C. prior to glycerol shock (15% glycerol for 3 minutes).

Two weeks following transfection, the cells were passaged. Thereafter, upon confluence the cells were passaged twice more. The appearance of transformed colonies occurred 6–8 weeks following original transfection in passage 3. The transformed colonies primarily contained epithelial looking cells, however, the morphology of cells in the foci was variable, some cells having a fibroblastic appearance. The transformation frequency of the cultured liver epithelial cells was 1×$10^{-4}$.

Attempts to clone single cells or foci from the original cultures resulted in death of the cells within 2–3 days. Thereafter, the flasks were serially passaged. The first two passages following foci appearance were passaged using the collagenase/Dispase solution used for original isolation, due to the extreme sensitivity of the cells to trypsin, and the remaining passages were done with a PVP-trypsin-EGTA solution. With increasing passage, the cells became more homogeneous, and at the 5th passage following transfection, virtually 100% of the cells expressed SV40 large T antigen.

With increasing passage the cells became more homogenous and at passage 8 virtually all the cells expressed SV40 large T antigen (as determined by indirect immunofluorescence), as well as cytokeratin 18 (a cytokeratin known to be expressed in normal human hepatocytes (Moll, R. W. et al, *Cell*, 31:11–24 (1982)).

All subsequent culture of the liver epithelial cells was in HGM, and these cells continued to proliferate for about 14 weeks at which time the culture senesced (i.e., entered crisis). Currently, 3 months after the cells entered crisis, colonies of dividing cells are present but have not been characterized.

To establish the expression of SV40 large T antigen, cells from passage 3 were grown on culture chamber slides and using indirect immunofluorescence, the culture was found to contain approximately 30% T antigen positive cells. By passage 5, the transformed liver cells were found to be uniformly positive for T antigen as determined by immunofluorescence. T antigen expression was maintained throughout subsequent culturing.

To establish that these transformed liver cells were epithelial, cells from early and late passages were examined for keratin expression using a general cytokeratin primary antibody and a fluorescent secondary antibody and found to be uniformly positive in both early (p.3) and late (p.11) passages.

Further examination using monoclonal antibodies against cytokeratin 18 and 19 was performed. At early and late passage the liver cells were positive for cytokeratin 18 but negative for cytokeratin 19. However, in late passages (p.10 and 11) some cells became positive for cytokeratin 19 as well as 18.

We examined the transformed liver epithelial cells for the production of proteins that are expressed by normal hepatocytes. The transformed cells were analyzed using fluorescent immunocytochemistry for expression of albumin, α1 antitrypsin and α2 macroglobulin. Albumin was detected in several colonies on the slide. Overall, approximately 20% of the cells taken from passage 9 were positive for albumin expression. When the cells were exposed to serum containing medium for 48 hrs prior to staining, more cells were positive for albumin expression (30–40%).

Materials used in this example include Dispase (0.5 U/mg) obtained from Boehringer Mannheim (Indianapolis, Ind.), collagenase (156 U/mg) from Worthington Biochemical Corp. (Freehold, N.J.) and standard tissue culture media and components from Biofluids Inc. (Rockville, Md.). Epidermal growth factor from Collaborative Research Inc. (Bedford, Mass.). Trypsin inhibitor, DNase and chemicals from Sigma Chemical Co. (St. Louis, Mo.) PFMR4 cell culture medium and factor free serum were prepared by Biological Research Faculty and facility (Ijamsville, Md.). Ex-cyte® V (Miles Laboratories, Diagnostics Division) a bovine lipoprotein, was used as a source of lipoprotein cholesterol, phospholipids and fatty acids with low endotoxin.

Serum free medium (growth-factor-inactivated serum) was prepared as follows:

Fetal calf serum (FCS; Flow Laboratories, Irvine, Scotland) was incubated with 100 mM dithiothreitol (DTT; Boehringer, Mannheim, GFR) for 2 hr at room temperature while stirring, resulting in turbid solution. The suspension was then dialyzed (molecular weight cutoff 8–10 kDa) overnight at 4° C. against a 50–100 fold excess of phosphate-buffered saline without $Ca^{++}$ and $Mg^{++}$ (PBS; 137 mM NaCl, 2.7 mM KCl, 6.5 MM $Na_2HPO_4$, 1.5 mM $KH_2PO_4$, pH 7.4). Subsequently iodoacetamide (Sigma, St. Louis, Mo., USA) was added at 5 g/liter, and the suspension incubated for another 2 hr at room temperature while stirring, followed by dialysis for 2 days against several aliquots of PBS, and an additional day against PBS containing in addition 0.9 mM $CaCl_2$ and 0.5 mM $MgCl_2$. Subsequently the SH-FCS was centrifuged at 25,000 g for 30 min at 4° C., and the supernatant again at 100,000 g for 60 min at 4° C. The clear supernatant was sterilized by passage through a Millex-GV 0.22 nm filter (Millipore, Bedford Mass., USA). Prepared from protocol in Van Zoelen et al, *J. Cell Physiol.*, 123:151–160 (1985)

The final serum-free medium (Lechner et al, *Methods in Cell Biol.*, 21, 195 (1980)) was prepared without arginine, calcium, glutamine, trace elements and iron. The medium was supplemented with:

| | |
|---|---|
| L-glutamine | 2 mM |
| insulin | 10 μg/ml |
| hydrocortisone | 0.2 μM |
| epidermal growth factor | 5.0 ng/ml |
| (Collaborative Research Inc. Bedford Mass.) | |
| transferrin | 10 μg/ml |
| phosphoethanolamine | 0.5 μM |
| cholera toxin | 25 ng/ml |
| triiodothyronine | 10 nM |
| retinoic acid | 10 nM |
| ornithine | 2 mM |
| $CaCl_2$ | 0.4 mM |
| glucose | 2.0 mg/ml |
| bovine pituitary extract | 7.5 μg/ml |
| "Ex-cyte"® V (Miles | 312 μg/ml |
| Diagnostics, Pentex® Products | |
| Kankakee, IL) (Ex-cyte is the brand name of an aqueous mixture of lipoprotein, cholesterol, phospholipids and fatty acids with low endotoxin). | |
| $FeSO_4.7H_2O$ | 2.7 μM |
| $ZnSO_4.7H_2O$ | 0.5 μM |
| Factor Free Serum (Van | 10% |
| Zoolen et al., J Cell Physiol., 123: 151 (1985)) | |
| $Na_2SeO_3$ | $3.0 \times 10^{-8}$ |
| $MnCl_2.4H_2O$ | 1.0 nM |
| $NaSiO_3.9H_2O$ | $5.0 \times 10^{-7}$ M |
| $(NH_4)_6Mo_7O_{24}.4H_2O$ | 1.0 nM |
| $NH_4VO_3$ | 5.0 nM |
| $NiSO_4.6H_2O$ | 0.5 nM |
| $SnCl_2.2H_2O$ | 0.5 nM |
| Gentamicin | 50 μg/ml |

The conditioned medium was isolated from high density monolayer cultures of HepG2 hepatoblastoma cells (American Type Tissue Collection #HB80-65) for 72 hours. This conditioned medium is added to normal HGM at a 35% concentration. Alternatively, human liver epithelial cells transformed by transfection with SV-40 DNA (NCI/NIH, patent pending) in contact with HGM may be used instead of HepG2.

EXAMPLE 3 (NORMAL CELLS)

Isolation of hepatocytes: Human hepatocytes were isolated by a combination of perfusion and digestion as previously described. Upon removal of human livers, the tissue was kept in ice cold L-15 medium and transported to the site of liver cell isolation. The hepatocytes were dissociated into cell suspensions by perfusing the liver with a calcium and magnesium free Hank's balanced salt solution containing 0.5 mM EDTA, and 0.05 M Hepes at 37° C., at a flow rate of 30–40 ml/min for 15 min.

The perfusate was then changed to a digestion solution containing collagenase (185–200 U/ml) at 37° C. at a flow rate of 30–40 ml/min for 20 min. The dissociated hepatocytes were purified from debris and red blood cells by three successive washes with L-15 and filtration through a 10 μ nylon filter. The hepatocytes were suspended in Waymouth's medium supplemented with 10% fetal bovine serum (FBS), 1 μg/ml insulin and 50 μg/ml gentamicin. The yield estimated counting the cells with a hemocytometer were 1–2×$10^7$ cells/g of liver tissue. Over 90% of the hepatocytes excluded trypan blue.

Primary culture of human hepatocytes: Following isolation, all hepatocytes were seeded into collagen coated flasks (Flow Lab, Rockville, Md.) in T-75 tissue culture flasks (Lux, Miles Scientific, Napperville, Ill.) at a density of 5×$10^5$ cells/flask. All flasks were maintained in a 3.5 humidified incubator at 37° C. Twenty-four hrs after isolation, the medium was changed to a semi-defined serum-free medium consisting of a basal medium PFMR4 made without arginine and supplemented with ornithine (2 mM), insulin (10 μg/ml), hydrocortisone (0.2 μM), epidermal growth factor (5 ng/ml), transferrin (10 μg/ml), phosphoethanolamine (0.5 μM), cholera toxin (25 ng/ml), triiodothyronine (10 nM), bovine pituitary extract (7.5 μg/ml) and factor-free serum (10%). After two weeks, this medium was supplemented (35%) with conditioned medium obtained by placing the medium described above in contact with high density cultures of human hepatoblastoma cell line (HepG2) for 72 hrs.

These cells continued to proliferate slowly for about 15 weeks at which time the culture scenesced. The original culture was subcultured four times and the cells underwent approximately 12 replications.

These cells were keratin positive and 20% retained the ability to produce albumin as demonstrated by immunocytochemistry.

EXAMPLE 4 (INFECTED CELLS)

Development of the THLE-2 Human Liver Cell Line

Normal human hepatocytes were isolated from non-cancerous individuals by combination of perfusion and digestion techniques previously described by Hsu et al, *In Vitro Cell Develop. Biol.*, 21:154–160 (1985). The left lobe of the liver was removed within two hours of cessation of cardiac function, immersed in ice cold Lebovitz-15 medium and transported to the site of liver cell isolation.

The hepatocytes were dissociated into cell suspensions by perfusing the liver with a calcium magnesium free Hank's balanced salt solution containing 0.5 mM EDTA, and 0.05 M Hepes at 37° C. at a flow rate of 30–40 ml/min for 15 min The perfusate was then changed to a digestion solution of collagenase (185–200 U/ml) at 37° C. at a flow rate of 30–40 ml/min for 20 min. The dissociated hepatocytes were purified from debris and red blood cells by three successive washes with L-15. The hepatocytes were suspended in Waymouth's medium supplemented with 10% fetal bovine serum, 1 μg/ml insulin and 50 μg/ml gentamicin. The yield was estimated by counting the cells with a hemocytometer, and was 1–2×$10^7$ cells/g of liver. Over 90% of the hepatocytes excluded trypan blue.

Following isolation, the cells (hepatocytes) were seeded into T-150 tissue culture flasks (Lux, Miles Scientific, Naperville, Ill.) whose surfaces had been coated with collagen (Michalopoulos, G. and Pitot, H., *Exp. Cell. Res.*, 94:70–73 (1975) (Flow Lab, Rockville, Md.) at 6000 cells/$cm^2$ using Waymouth's medium with insulin and gentamicin as previously described.

Twenty-four hours after the initial seeding, the medium was changed to a serum-free medium LCM (Liver Cell Medium) described below. The medium is made from PFMR4 basal medium (Kaighn, M. E. et al, *Proc. Natl. Acad. Sci.*, 78:5673–5676 (1981)) without arginine and supplemented with ornithine (2 mM), insulin (10 μg/ml), hydrocortisone (0.2 μM), epidermal growth factor (5 ng/ml), transferrin (10 μg/ml), phosphoethanoloamine (0.5 mM), cholera toxin (25 ng/ml), triiodothyronine (10 nM), bovine pituitary extract (7.5 μg/ml) and factor serum (10%). Additionally, this medium was supplemented (35%) with conditioned medium obtained by placing the LCM described above in contact with high density cultures of human hepatoblastoma cell line (HEPG2) for 72 hours.

One week following the original isolation, the liver cells were infected with an amphotropic SV40-T antigen virus. This virus was produced using a psi 2 SV40-T antigen packaging cell line received from R. Mulligan (Jat, P. et al, *Molec. Cell. Biol.*, 6:1209–1217 (1986)). The psi 2 cells were grown in DMEM medium supplemented with 10% fetal bovine serum. Supernatant of confluent cultures of these cells was employed to infect the amphotrophic packaging cell line PA317 (Miller, A. D., *Molec. Cell Biol.*, 2:2895–2902 (1986)). Subsequently, the PA317 cells were selected for neomycin resistance and 10 resistant clones were expanded for the isolation of amphotrophic virus. For the virus isolation, the PA317 clones were grown in DMEM medium supplemented with 10% fetal bovine serum, grown to confluence and, twenty-four hours prior to collection, the medium was changed to PC-1 (Ventrex Laboratories, Inc., Portland, Me.). The collected virus was titered on NIH3T3 cells in the presence of 8 μg/ml polybrene.

Primary cultures of hepatocytes were infected in PC-1 medium supplemented with 8 μg/ml polybrene for 2 hrs. with virus obtained from seven PA317 clones releasing SV40 T-antigen virus. Afterwards, the cultures were washed and incubated with LCM medium. The cells infected with SV40 T-antigen virus grew very well for 6 weeks at which time they began to decrease their population doubling rate. At this time the LCM medium was supplemented with arginine and 0.25% fetal bovine serum. The infected liver cells have undergone more than 50 population doublings, have a doubling time of 24 hrs, and express both cytokeratin 18 and T-antigen. The cells are currently still growing and have been deposited at the American Type Culture Collection (12301 Parklawn Drive, Rockville, Md.) (ATCC designation CRL 10149) in accordance with the conditions of the Budapest Treaty.

UTILITY

Examples of uses

UTILITY OF CELL LINES (1) Identification of potential chemotherapeutic drugs: These cells are useful for screening chemicals suitable for the treatment of cancer and related diseases, by growing them in vitro in medium containing the chemical to be tested and then, after a suitable period of exposure, determining whether and to what extent cytotoxicity has occurred, e.g. by trypan blue exclusion assay or related assays (Paterson, *Methods Enzymol*, 58:141 (1979)), or by growth assays such as colony forming efficiency (MacDonald et al, *Exp. Cell. Res.*, 50:417 (1968)), all of which are standard techniques well known in the art.

(2) Investigation of the controls of differentiation and identification of chemical and biological agents that induce terminal differentiation. Chemical and biological substances are screened for their ability to induce terminal differentiation by adding them to the growth medium of these liver cells and then after a suitable period of time, determine whether a complex of changes, including cessation of DNA synthesis, and production of liver specific proteins (as determined by in situ hybridization techniques) occurs. Induction of terminal differentiation may be an effective way of controlling the growth of cancer.

(3) Studies of metabolism of carcinogens and other xenobiotics: Carcinogens and other xenobiotics may be added to the growth medium of these cells and the appearance of metabolic products of these compounds may be monitored by techniques such as thin layer chromatography or high performance liquid chromatography and the like, and the interaction of the compounds and/or their metabolites with DNA is determined.

(4) Studies of DNA mutagenesis: Substances known or suspected to be mutagens may be added to the growth medium of the cells and then mutations may be assayed, e.g., by detection of the appearance of drug resistant mutant cell colonies (Thompson, Methods Enzymol, 58:308, 1979).

(5) Studies of chromosome damaging agents: Substances known or suspected to cause DNA or chromosomal damage may be added to the culture medium of these cell lines, and then the extent of chromosomal damage may be measured by techniques such as measurement of the frequency of sister chromatic exchange (Latt et al. In: Tice, R. R. and Hollaender, A., Sister Chromatic Exchanges, New York: Plenum Press, pp, 11 ff. (1984)).

Protocols for Detection of BrdUrd Substitution into Metaphase Chromosomes 1. 33258 Hoechst Fluorescence (S. A. Latt et al., *Proc. Natl. Acad. Sci. USA* 70:3395 (1973); S. A. Latt et al., *Cytochem.* 25:913 (1977))

a. Staining. Slides are successively dipped in PBS (0.14 M NaCl, 0.004 M KCl, 0.01 M phosphate, PH 7.0) (5'), 0.5 µg/ml 33258 Hoechst in PBS (10'), PBS (1'), PBS (5'), and $H_2O$ (two to three changes). Stock solutions of dye (50 µg/ml) in $H_2O$ can be stored at 4° C. in the dark for at least 2 weeks. Samples of 33258 Hoechst were originally obtained from Dr. H. Loewe, Hoechst AG, Frankfurt, Germany, although the dye can now be purchased from Calbiochem.

b. Observation. Microscopic observation of 33258 Hoechst fluorescence is guided by the position of the high wavelength absorption band of the dye-DNA complex (maximal near 350 nm and appreciable up to or slightly beyond 425 nm). While excitation under dark-field conditions is certainly possible, excitation with incident illumination, using a UG-1 (360 nm peak) bandpass and TK 400 (reflect ≦400 nm) dichroic mirror is especially convenient and effective. A 460 nm high wavelength pass filter in the observation pathway removes most unwanted exciting light from the fluorescence, which peaks near 475 nm.

For optimal quenching of dye fluorescence by incorporated BrdUrd, the slides are mounted in a buffer of moderate ionic strength at or slightly above neutrality, for example, pH 7.5 McIlvaine's buffer. Primarily because of the specificity of the stain, under these conditions, for (A-T rich) DNA, and because the free dye has very weak fluorescence, slides observed as described above show little background fluorescence. However, the fluorescence of 33258 Hoechst bound to BrdUrd-substituted chromatin fades rapidly, and photography requires speed. Using a microscope with incident illumination, acceptable photographs can be obtained in 5–10 sec (e.g., Kodak Tri-X film). Reduction of the mounting medium pH shifts the dye fluorescence color from blue toward green or yellow, and the fluorescence fades less rapidly; but specific quenching due to BrdUrd substitution is decreased.

2. 33258 Hoechst plus Giemsa (adapted from P. Perry and S. Wolff, *Nature* 261:156 (1974); S. Wolff (1981), Measurement of sister chromatid exchange in mammalian cells. In DNA Repair: A Laboratory Manual of Research Procedures, Volo 1, Part B (E. C. Friedberg and P. C. Hanawalt, Eds.), Dekker, N.Y.)

a. Staining. Slides are stained with $10^{-4}$ M 33258 Hoechst in one-third strength PBS (or a comparable buffer with a pH near 7). A cover slip is applied and the slides are then placed in a Petri dish containing excess buffer to ensure that the slides remain moist, and the slides are exposed to light for a period of time that depends on the illuminating conditions. For example, approximately 6–12 hours of exposure is sufficient after the slides are positioned 6 cm from a Sylvania 20 watt cool white bulb (Latt et al., *Cytochem.* 25:913 (1977)). The slides are then rinsed in $H_2O$, incubated at 65° C. in 2 x SSC buffer (0.30 M NaCl, 0.03 M Na citrate, pH7) for 15 min., rinsed thoroughly with $H_2O$, and stained with Giemsa as before. Contrast can be heightened by increasing the time during which slides are exposed to light.

b. Observation. For photographs slides can be mounted in a standard embedding mediums or immersion oil can be applied directly to the slide without a cover slip. A 544 nm interference filter can be used to enhance contrast, and the optical image is recorded using, for example, High Contrast Copy film.

While there is a wealth of methods for differentiating between sister chromatids, a few simple techniques can suffice for most studies. Representative techniques, employing 33258 Hoechst fluorescence or 33258 Hoechst followed sequentially by illumination, SSC incubation, and Giemsa staining are detailed. Procedural details for SCE analysis have also been presented by (Wolff, S. (1981), Measurement of sister chromatid exchange in mammalian cells. In DNA Repair: A Laboratory Manual of Research Procedures, Vol. 1, Part B (E. C. Friedberg and P. C. Hanawalt, Eds.), Dekker, N.Y.) It should be noted that other techniques, related to those described above, can work equally well and DNA damage can be determined by the measurement of unscheduled DNA synthesis (Mirsalis, J. C. Banbury report vol. 13, p 83–99 (1982). The procedures for this assay have been previously described (J. C. Mirsalis et al. *Environ. Mutagen* 4 (in press)). Fischer-344 rats are treated with chemicals by a suitable route of exposure, and at selected times after treatment, their livers are perfused with a collagenase solution. A single-cell suspension of hepatocytes is obtained by combing out the cells of the perfused liver into a petri dish containing collagenase solution, Cells are seeded into culture dishes containing coverslips and Williams Medium E supplemented with 10% fetal bovine serum, allowed to attach to the coverslips, and incubated with a solution of 10 μCi/ml $^3$H-thymidine ($^3$H-dT) for 4 hours. Following overnight incubation (14–18 hr) in 0.25 mM unlabeled thymidine, cells are swelled, fixed, and washed; coverslips are mounted on microscope slides and dipped in Kodak NTB-2 photographic emulsion. After being exposed for 12–14 days, slides are developed and the cells are stained.

Quantitative autoradiographic grain counting is accomplished using a colony counter interfaced to a microscope via a TV camera; data are fed directly into a computer. Fifty morphologically unaltered cells from a randomly selected area of the slide are counted. The highest count from three nuclear-sized areas over the cytoplasm and adjacent to the nucleus is subtracted from the nuclear count to give the net grains/nucleus (NG). The percentage of cells in repair indicates the extent of damage throughout the liver and is calculated as those cells exhibiting>5 NG.

(6) Studies of malignant transformation by chemical, physical and viral agents, and transferred genes including oncogenes and high molecular weight genomic DNA from tumors, using standard assays such as anchorage independent growth or tumor formation in athymic nude mice. For example, a cloned viral oncogene N-ras (an oncogene present in many liver cell cancers) can be introduced into the liver epithelial cells using strontium phosphate transfection. The subsequent ability of the newly transfected cells to form tumors in mice as well as grow in an anchorage-independent fashion can be assessed.

(7) Use of cells altered by transfer of oncogenes as in paragraph (6) above to screen for potential chemotherapeutic agents (by the techniques described in paragraph (1) above) especially those which may be specific for cells transformed by the activation of particular oncogenes or combination of oncogenes.

(8) Studies of cellular biochemistry, including changes in intracellular pH and calcium levels, as correlated with cell growth and action of exogenous agents including but not limited to those described in paragraphs (1) through (7) above. To study intracellular pH and calcium levels, cells in suitable culture vessels are exposed to fluorescent indicator dyes and then fluorescence emissions are detected with a fluorescence spectrophotometer (Grynkiewicz et al, *J. Biol. Chem.*, 260:3440–3450 (1985)).

(9) Studies of cellular responses to growth factors and production of growth factors: Identification and purification of growth factors important for growth and differentiation of human liver epithelial cells. These cells are particularly useful for such an application since they grow in serum-free media. Therefore, responses to growth factors can be studied in precisely defined growth medium and any factors produced by the cells may be identified and purified without the complication of the presence of serum.

(10) Use of recombinant DNA expression vectors to produce proteins of interest. For example, the gene encoding a protein of therapeutic value may be recombined with controlling DNA segments (i.e. containing a promoter with or without an enhancer sequence), transferred into the cell (e.g., by strontium phosphate transfection) and then the protein produced may be harvested from the culture supernatant or a cellular extract by routine procedures well known in the art.

(11) Studies of intracellular communication e.g., by dye scrape loading assays, to determine whether the cells growing in vitro have the ability to communicate via gap junctions. The cultures may be scraped, e.g., with a scalpel, in the presence of a fluorescent dye in the growth medium. Cells at the edge of the wound are mechanically disrupted and therefore take up dye; whether intercellular communication has occurred may be ascertained by determining whether cells distant from the wound also contain dye.

(12) Characterization of cell surface antigens: The cells are incubated with an antibody against the cell surface antigen of interest, and then reacted with a second antibody which is conjugated to a fluorescent dye. The cells are then evaluated using a fluorescence activated cell sorter to determine whether they are fluorescent and therefore posses the cell surface antigen.

(13) Cell—cell hybrid studies for identification of tumor suppressor activity (Stranbridge et al, *Science,* 215:252–259 (1982)). To determine whether these cell lines contain tumor suppressor genes, they are fused to malignant tumor cells. The presence of tumor suppressor genes is indicated by loss of malignancy e.g., as detected by loss of ability to form tumors in athymic nude mice, in the hybrid cells.

(14) Identification of novel genes, including transforming genes in the naturally occurring cancer described in paragraph (6) above, growth factor genes as described in paragraph (9) above, tumor suppressor genes as described in paragraph (13) above, using standard molecular biological techniques (Davis et al, *Methods in Molecular Biology*, New York: Elsevier (1986)) and techniques such as cDNA subtraction cloning and similar processes.

(15) Growth of replicating hepatitis virus (as e.g., HBV, non-A non-B, HAV and other livertropic virus, e.g., CMV). Establishment of a clonal cell line of human liver epithelial cells containing replicating Hepatitis virus using methods of transfection established for human liver cancer cells lines (Sells, M. A. et al, *Proc. Natl. Acad. Sci.,* 84:444–448). Using human liver epithelial lines which contain HBV, the ability of HBV alone as well as in conjunction with chemical liver carcinogens such as aflatoxin B, can be evaluated for malignant transformation using anchorage independent growth assays as well as growth in athymic nude mice. Cell—cell hybrid techniques similar to those in paragraph (13) can be used to evaluate possible inactivation of tumor suppressor genes by fusion with malignant cells before and after HBV transfection.

The screening kits are easily assembled as other screening kits containing cell lines with other conventional components and labeling instructions for performing the test.

(16) The transformed or transfected cells may be used as a way of expanding cells for liver transplant and liver function assist devices, both implanted and extracorporeal. Also, these cells can have additional genes transfected/ infected into them for organ transplant for therapy of inherited metabolic disorders, especially those diseases associated with hepatic degradation (i.e., certain diseases are due to a deletion or abnormality of a particular gene). This gene could then be transfected into our cells, and the cells then expanded for organ transplant.

(17) Studies of cytotoxicity of drugs, carcinogens, xenobiotics: Drugs, carcinogens, xenobiotics may be added to the growth medium of the cells and the viability of the cells as a function of time of exposure may be ascertained using dye exclusion, enzyme leakage, colony forming efficiency, etc. assays.

(18) Studies of putative tumor promoters and agents that may inhibit tumor promotion: Putative tumor promoters may be added to the growth medium of the cells and the state of transformation of the cells as a function of time of exposure may be ascertained using anchorage independence growth, matrix invasion, cell to cell communication assays and/or nude mice tumorigenicity assays. Tumor promoters may be added with putative anti-tumor promoting agents to the growth medium of the cells and the state of transformation of the cells as a function of time of exposure may be ascertained using anchorage independence growth, matrix invasion, cell to cell communication assays and/or nude mice tumorigenicity assays.

(19) Studies of liver parasites: The cultured cells could prove efficacious for studying the life cycle of parasites that invade hepatocytes.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A continuous human liver epithelial cell line isolated from normal adult human liver epithelial cells wherein cells of said continuous cell line have the following properties:

i) non-tumorigenic;

ii) express SV40 T antigen;

iii) 20% of the cells express albumin when grown in a serum-free medium; and iv) 30 to 40% of the cells express albumin when grown in a medium containing serum.

2. The cell line of claim 1, wherein said T antigen is expressed from DNA introduced into the genome of said cells by infection with an amphotrophic retrovirus containing RNA encoding SV40 T antigen.

3. A kit for screening carcinogenic or chemotherapeutic agents comprising: a container containing a continuous, non-tumorigenic, human liver epithelial cell line or derivative thereof according to claim 1.

4. A method for testing carcinogenicity of a compound, comprising culturing the cell line of claim 1 with a compound suspected of being carcinogenic; and assessing at least one of the growth properties selected from the group consisting of anchorage dependence of proliferation and tumorigenicity in vivo in athymic nude mice, wherein anchorage independence of proliferation or tumorigenicity in vivo in athymic nude mice is indicative of carcinogenicity of said compound.

5. A method for testing antineoplastic activity of a compound, comprising culturing the cell line of claim 1 with a potential antineoplastic agent and assaying DNA synthesis, wherein cessation of DNA synthesis is indicative of antineoplastic activity of said compound.

6. A method for testing a compound for chromosome-damaging activity, comprising culturing the cell line of claim 1 with a compound suspected of damaging chromosomes and assaying at least one measure of chromosome damage selected from the group consisting of the frequency of sister chromatid exchange and unscheduled DNA synthesis, wherein an increase in the frequency of sister chromatid exchange or an increase in the amount of unscheduled DNA synthesis is indicative of chromosome-damaging activity of said compound.

7. The cell line of claim 1, which has undergone 50 population doublings.

8. The cell line of claim 1, which further expresses cytokeratin 18.

9. The cell line of claim 1, which has a doubling time of 24 hours.

10. A method for transforming normal adult human liver epithelial cells to create a continuous human liver epithelial cell line, which comprises:

culturing normal adult human liver epithelial cells in a cell culturing medium consisting essentially of an amount of the following ingredients effective to sustain proliferation of normal adult human liver epithelial cells:

an effective amount of ornithine to allow proliferation of normal adult human liver epithelial cells;

growth factor inactivated serum;

retinoic acid in an amount of 1 to 300 nM;

an effective amount of calcium ions high enough to promote cell proliferation but low enough to avoid cellular differentiation between 0.2 and 1 mM;

an effective cell proliferation promoting amount of glucose;

an effective amount of insulin to aid cells in glucose uptake;

an effective cell proliferation promoting amount of hydrocortisone;

an effective amount of epidermal growth factor to bind epidermal growth factor receptors on cells;

an effective amount of transferrin to increase DNA synthesis in cells;

an effective amount of cholera toxin to increase DNA synthesis in cells;

an effective amount triiodothyronine to increase DNA synthesis in cells;

an effective proliferation promoting amount of mammalian hormones;

an effective cell proliferation promoting amount of medium conditioned by HepG2 hepatoblastoma cells;

said medium containing no arginine; and contacting said cells with a vector containing an SV40-T antigen gene to effect transformation and to produce a continuous human liver epithelial cell line.

11. The method of claim 10, wherein said normal adult human liver epithelial cells are contacted with an amphotrophic retrovirus containing RNA encoding SV40 T-antigen.

12. A continuous human liver epithelial cell line consisting essentially of cells tranformed by the method of claim 10.

13. The method of claim 10, wherein said culturing medium consists essentially of:

water;

ornithine in an amount of about 2 mM;

chemically denatured serum in an amount of about %10;

an effective cell proliferation promoting amount of all of the essential amino acids;

an effective cell proliferation promoting amount of water soluble vitamins;

an effective cell proliferation promoting amount of coenzymes;

an effective cell proliferation promoting amount of sodium ions;

an effective amount of calcium ions high enough to promote cell proliferation but low enough to avoid cellular differentiation between 0.2 and 1 mM;

an effective cell proliferation promoting amount of glucose;

insulin in an amount of 1 to 10 μg/ml hydrocortisone in an amount of 0.05 to 1 μM;

epidermal growth factor in an amount of 1 to 25 ng/ml;

transferrin in an amount of 1 to 10 μg/ml;

cholera toxin in an amount of 5 to 50 ng/ml;

triiodothyronine in an amount of 1 to 100 nM;

retinoic acid in an amount of 1 to 300 nM;

an effective amount of a mammalian pituitary extract to provide hormones and mitogenic factors necessary for culturing normal adult human liver epithelial cells;

an effective cell proliferation promoting amount of medium conditioned by HepG2 hepatoblastoma cells;

an effective cell proliferation promoting amount of lipoprotein, cholesterol, phospholipids, and fatty acids with low endotoxin; and an effective amount of buffer to maintain the pH between 6.7 and 7.6.

14. A continuous human liver epithelial cell line consisting essentially of cells transformed by the method of claim 13.

15. A continuous human liver epithelial cell line isolated from normal adult human liver epithelial cells wherein cells of said continuous cell line have the following properties:

i) non-tumorigenic;

ii) express SV40 T antigen;

iii) 20% of the cells express albumin when grown in a serum-free medium; and iv) 30 to 40% of the cells express albumin when grown in a medium containing serum; that is the cell line deposited as ATCC CRL 10149.

16. A method for proliferative culture of normal adult human liver epithelial cells, which comprises:

culturing normal adult human liver epithelial cells in a cell culturing medium, wherein said culturing medium sustains proliferation of normal adult human liver epithelial cells and consists essentially of the following ingredients in about the amounts indicated:

| INGREDIENT | mg/liter |
|---|---|
| L-cystine.2HCl | 47.0 |
| L-histidine | 41.9 |
| L-isoleucine | 7.9 |
| L-leucine | 26.2 |
| L-lysine.HCl | 73.0 |
| L-methionine | 9.0 |
| L-phenylalanine | 9.9 |
| L-threonine | 23.8 |
| L-tryptophan | 4.1 |
| L-tyrosine.2Na.2H$_2$O | 15.7 |
| L-valine | 23.4 |
| Nonessential Amino Acids | |
| L-alanine | 17.8 |
| L-asparagine.H$_2$O | 30.0 |
| aspartic acid | 26.6 |
| glutamic acid | 29.4 |
| L-glycine | 15.0 |
| L-proline | 69.1 |
| L-serine | 21.0 |
| Amino Acid Derivatives | |
| putrescine.2HCl | 0.32 |
| Water Soluble Vitamins and Coenzymes | |
| d-biotin | 0.07 |
| folic acid | 1.32 |
| DL-A-lipoic acid (thioctic) | 0.21 |
| nicotinamide | 0.04 |
| D-pantothenic acid | 0.24 |
| pyridoxine.HCl | 0.06 |
| riboflavin | 0.04 |
| thiamine.HCl | 0.34 |
| vitamin B12 (Cyanocobalamine) | 1.36 |
| Carbohydrates/Derivatives | |

-continued

| INGREDIENT | mg/liter |
|---|---|
| pyruvic acid | 174.0 |
| sodium acetate | 295.6 |
| Nucleic Acid Derivatives | |
| hypoxanthine | 4.1 |
| thymidine | 0.7 |
| Lipids/Derivative | |
| choline chloride | 14.0 |
| inositol | 18.0 |
| Bulk Inorganic Ions (Salts) | |
| NaCl | 5844.0 |
| KCl | 283.3 |
| Na$_2$HPO$_4$ | 126.4 |
| KH$_2$PO$_4$ | 58.5 |
| MgSO$_4$ | 19.3 |
| MgCl$_2$.6H$_2$O | 105.7 |
| Inorganic Trace Elements | |
| CuSO$_4$.5H$_2$O | 0.002 |
| Buffers and Indicators | |
| NaHCO$_3$ | 1176.0 |
| HEPES buffer | 7149.0 |
| phenol red | 1.1 |
| L-glutamine | 2 mM |
| Growth factors | |
| insulin | 10 µg/ml |
| hydrocortisone | 0.2 µM |
| epidermal growth factor | 5.0 ng/ml |
| transferrin | 10 µg/ml |
| Other ingredients | |
| phosphoethanolamine | 0.5 µM |
| cholera toxin | 25 µg/ml |
| triiodothyronine | 10 nM |
| retinoic acid | 10 nM |
| ornithine | 2 mM |
| CaCl$_2$ | 0.4 mM |
| glucose | 2.0 mg/ml |
| bovine pituitary extract | 7.5 µg/ml |
| "Ex-cyte ®" | 312 µg/ml |
| FeSO$_4$.7H$_2$O | 2.7 µM |
| ZnSO$_4$.7H$_2$O | 0.5 µM |
| Chemically denatured Fetal Bovine Serum | 10% |
| Na$_2$SeO$_3$ | $3.0 \times 10^{-8}$M |
| MnCl$_2$.4H$_2$O | 1.0 nM |
| Na$_2$SiO$_3$.9H$_2$O | $5.0 \times 10^{-7}$M |
| (NH$_4$)$_6$Mo$_7$O$_{24}$.4H$_2$O | 1.0 nM |
| NH$_4$VO$_3$ | 5.0 nM |
| NiSO$_4$.6H$_2$O | 0.5 nM |
| SnCl$_2$.2H$_2$O | 0.4 nM |
| Gentamicin | 50 µg/ml |

17. The method of claim 16, wherein the concentration of calcium ions if 0.4 mM.

18. The method of claim 16, wherein said normal adult human liver epithelial cells are infected with an amphotrophic retrovirus containing RNA encoding SV40-T antigen.

19. A continuous human liver epithelial cell line isolated using the method of claim 18.

20. A method of assaying a compound for antineoplastic activity which comprises; culturing the cell line of claim 56 in a medium containing a potential antineoplastic composition; culturing said cell line in a medium lacking the potential antineoplastic composition; and comparing expression of at least one liver-specific protein by the cell line cultured in the medium containing the composition with the expression of said liver-specific protein or proteins by the cell line cultured in the medium lacking the composition.

21. The method of claim 20, wherein said liver-specific protein or proteins are selected from the group consisting of albumin, α2 macroglobulin, α-fetoprotein, α-1-antitrypsin, cytokeratin 18 and cytokeratin 19.

22. A continuous human liver epithelial cell line isolated from normal adult human liver eptithelial cells, wherein cells of said continuous cell line have the following properties:

i) non-tumorigenic;
ii) life span in vitro of at least 40 population doublings;
iii) express SV40 T antigen;
iv) 20% of the cells express albumin when grown in a serum-free medium; and
v) 30 to 40% of the cells express albumin when grown in a medium containing serum.

* * * * *

UNITED STATES PATENT AND TRADEMARK OFFICE
CERTIFICATE OF CORRECTION

PATENT NO. : 5,529,920
DATED : June 25, 1996
INVENTOR(S) : Cole et al.

It is certified that error appears in the above-indentified patent and that said Letters Patent is hereby corrected as shown below:

Column 16, line 33, after "amphotrophic virus.", please insert the following paragraph:

--One of the expanded clonal cell lines was designated PA317-T for purposes of deposit and was deposited, under the terms and conditions of the Budapest Treaty, in the American Type Culture Collection, 12301 Parklawn Drive, Rockville, MD 20852, on April 5, 1996, under the accession number CRL-12080.--

Signed and Sealed this

Tenth Day of December, 1996

Attest:

BRUCE LEHMAN

Attesting Officer

Commissioner of Patents and Trademarks